(12) United States Patent
Murray et al.

(10) Patent No.: US 6,872,786 B2
(45) Date of Patent: Mar. 29, 2005

(54) MOLECULARLY IMPRINTED POLYMERIC SENSOR FOR THE DETECTION OF EXPLOSIVES

(75) Inventors: George M. Murray, Columbia, MD (US); Bradley M. Arnold, Columbia, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 10/182,518

(22) PCT Filed: Apr. 10, 2001

(86) PCT No.: PCT/US01/11562

§ 371 (c)(1),
(2), (4) Date: Jul. 30, 2002

(87) PCT Pub. No.: WO01/77664

PCT Pub. Date: Oct. 18, 2001

(65) Prior Publication Data

US 2003/0027936 A1 Feb. 6, 2003

Related U.S. Application Data

(60) Provisional application No. 60/195,934, filed on Apr. 10, 2000.

(51) Int. Cl.[7] ............................................... C08F 26/06
(52) U.S. Cl. ................... 525/326.7; 525/384; 73/35.14; 356/478
(58) Field of Search ............................. 525/384, 326.7; 73/35.14; 356/478

(56) References Cited

U.S. PATENT DOCUMENTS 5,360,880 A * 11/1994 Pashley et al. .............. 526/213

FOREIGN PATENT DOCUMENTS

JP          56049712          6/1981

OTHER PUBLICATIONS

Polymeric organic–inorganic hybrid material containing Iron (III) perphyrin using sol–gel process, XP–002190286, Journal of Non–Crystalline Solids 247 (1999) 146–152, K.J. Cluffl, et al.

Molecular Imprinting: at the edge of the third millenium, Trends in Biotechnology vol. 19, No. 1 Jan., Sergey A. Piletsky, Susan Alcock and Anthony P.F. Turner.

Polymer–Based Lanthanide Luminescent Sensor for Detection of the Hydrolysis Product of the Nerve Agent Soman in Water, XP–008825699, Analytical Chemistry, vol. 71, No. 2, Jan. 15, 1999, Amanda L. Jenkins, O. Manuel Uy and George M. Murray.

* cited by examiner

Primary Examiner—William K. Cheung
(74) Attorney, Agent, or Firm—Francis A. Cooch (57) ABSTRACT

A molecularly imprinted polymeric explosives sensor is provided which possesses selective binding affinity for explosives, such as 2,4,6-trinitrotoluene (TNT) and 1,3,5-trinitrobenzene (TNB). The polymeric sensor incorporates a porphyrin which undergoes a detectable change in absorption and/or emission of electromagnetic radiation when the polymer is exposed to explosives.

2 Claims, 5 Drawing Sheets

MOLECULARLY IMPRINTED POLYMERIC SENSOR FOR THE DETECTION OF EXPLOSIVES

CROSS-REFERENCE TO RELATED APPLICATIONS

This application claims the benefit of prior filed now abandoned U.S. application Ser. No. 60/195,934, filed on Apr. 10, 2000.

BACKGROUND OF THE INVENTION

1. Field of the Invention

The present invention relates to a molecularly imprinted polymeric sensor having selective binding affinity for a target molecule which comprises an explosive chemical. More particularly, this invention is directed to a molecularly imprinted polymer containing therein porphyrin moieties possessing cavities which selectively bind the target molecule when the polymer is exposed to environments containing the target molecule. Upon binding of the target molecule, the polymer undergoes a detectable adsorption and emission of electromagnetic radiation in the red or near infrared (IR) region.

2. Description of the Related Art

Remote chemical sensors must fulfill two goals: (1) the development of a specific chemical recognition element that allows a molecule, or class of molecule, to be identified, and (2) a means of signal transduction in which the presence of the molecule causes a measurable change in a physical property of the material. Although these goals are not always separable, the successfull design of chemical sensors requires that both be satisfied.

Most transduction approaches are based on optical, resistive, surface acoustic wave, or capacitive measurements. These well-developed methods dominate largely because of their ease of operation, sensitivity, and cost. The chemical recognition elements in these detectors, however, lag far behind. Indeed, most reports on chemical sensors suggest that many other devices could be fabricated in only suitable chemical recognition units were available. The missing element is a general approach to chemical recognition that allows the rational design and assembly of materials in a stable and reusable form. The present invention solves this problem based on the fabrication of molecularly imprinted polymers (MIPs).

An MIP is generally described as a plastic cast or mold of the molecule of interest, where recognition is based on shape, much like a lock and key. MIPs are made by adding the molecule of interest to a solution of binding molecules that can be chemically incorporated into a polymer (see FIG. 1). These binders usually have an affinity for the target and form a complex.

The interactions that hold these complexes together include Π—Π interactions, hydrogen bonding, metal-ligand binding, and even covalent bond formation, but they must be reversible. The binder must also have a chemical functionality that allows it to be irreversibly bound to polymers. Vinyl groups are a common functional group used to prepare many polymers, e.g., polyethylene, polystyrene, polyvinylalcohol, and polyvinylchloride. The target-binder complex is dissolved in excess matrix monomer (for example, styrene) and possibly other additives such as a cross-linker and porogens (solvents).

In a typical sensor fabrication, a solid plastic mass, consisting of the matrix and binder, is obtained which is chemically bound to the polymer/cross-linker matrix and the target molecule. Removal of the target is possible since it is reversibly bound to the binder. The cavity it leaves behind is permanently shaped like the target.

Methods for the detection of explosives and explosive residues require complex analytical instruments such as liquid or gas chromatographs coupled with mass spectroscopic or chemiluminescent detection. The associated instrumentation is usually large, expensive, difficult to maintain and requires skilled operators. If laboratory analysis is necessary, extensive documentation is needed for sample transport, increasing the possibility of sample contamination. Immunoassay tests are available for some explosives, but these are cumbersome and have short shelf lives.

SUMMARY OF THE INVENTION

The present invention provides a molecularly imprinted polymer containing incorporated therein porphyrin moieties which selectively bind a target molecule which comprises an explosive chemical. The molecularly imprinted polymer is formed by the steps comprising:

(A) providing the reaction product of (i) a polymerizable porphyrin derivative and (ii) a target molecule comprising an explosive chemical;

(B) copolymerizing the reaction product of step (A) with monomer and crosslinking agent to form a polymer; and (C) removing the target molecule from the polymer, said polymer exhibiting selecting binding affinity for the target molecule and undergoing a detectable change in absorption and/or emission of electromagnetic radiation when the target molecule binds thereto.

Figure 3:
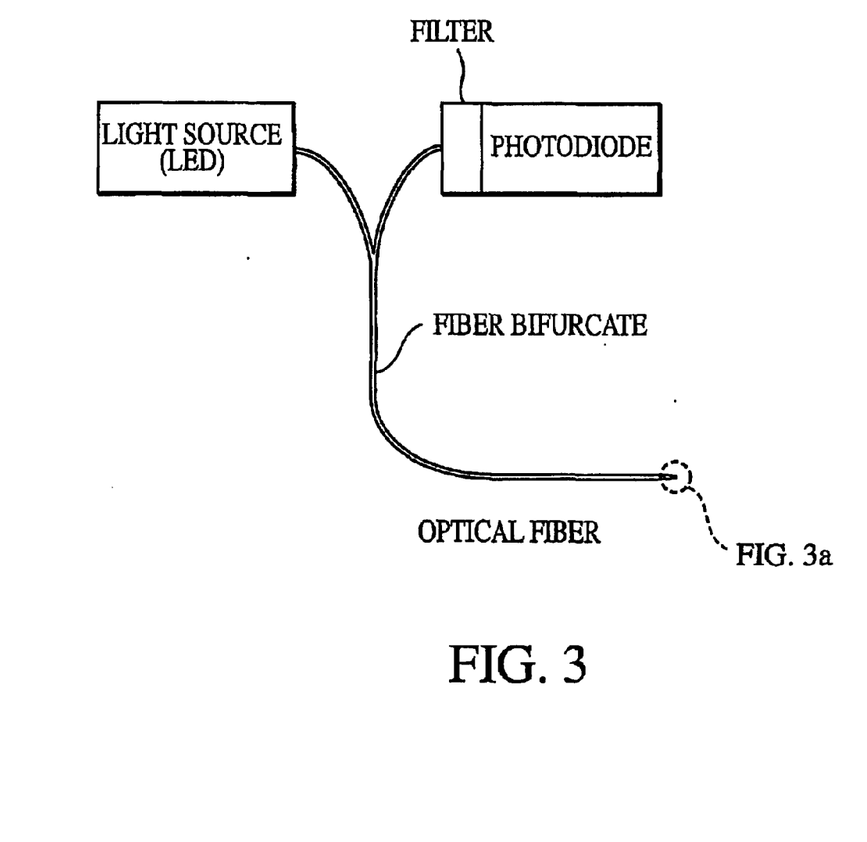
FIG. 3 is a schematic drawing of an optical sensor of the present invention.
Figure 3A:
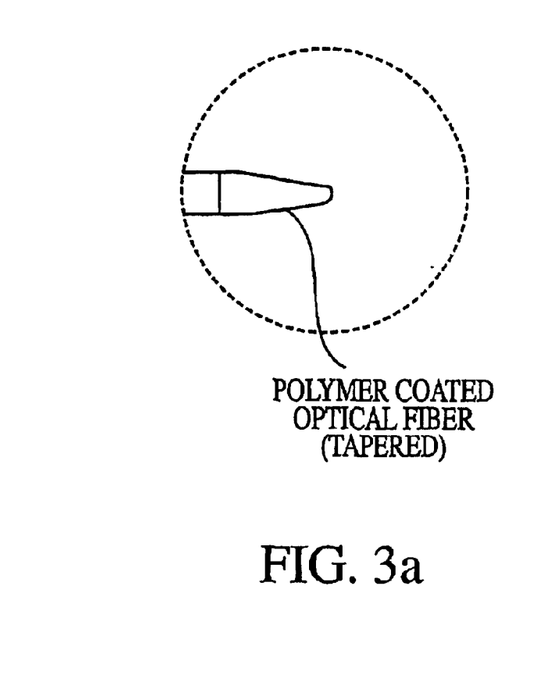
Figure 4:
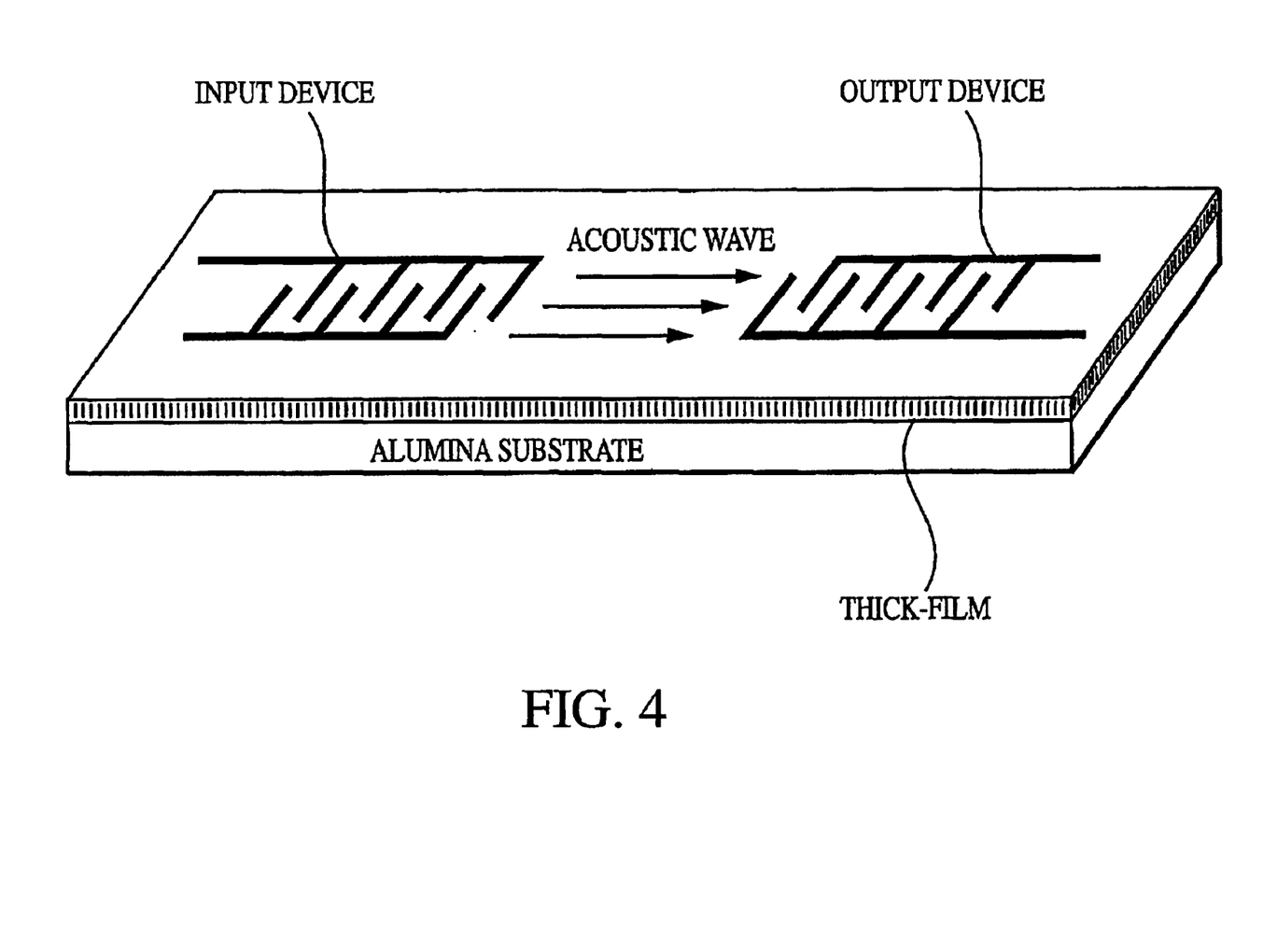
FIG. 4 is a schematic drawing of a surface acoustic sensor of the present invention.

Also provided in accordance with the invention is a spectroscopic sensor comprising the molecularly imprinted polymer of the invention. The sensor may comprise a fiber optic or other waveguide sensor for detecting the presence of target molecules comprising explosives such as TNT and TNB, as well as analogs and degradents thereof in a fluid, the sensor comprising:

at least one optical fiber means having a proximal end and a distal end for transmitting light energy, the proximal end being disposed within a probe housing, the molecularly imprinted polymer of the invention disposed on or bonded to the distal end of the optical fiber means, wherein the polymer is capable of chemically binding with said target molecule, light source means for generating excitation energy, said light source means operatively associated with said optical fiber means such that said excitation light passes through said optical fiber means, and detection means operatively associated with said optical fiber means, for detecting an emission and/or absorption signal generated by said polymer. As used herein, the term "light" refers to optical radiation, whether ultraviolet, visible or infrared with the porphyrin-containing polymers principally absorbing in the rear IR region. FIG. 3 depicts a sensor having the features of this embodiment.

Figure 2:
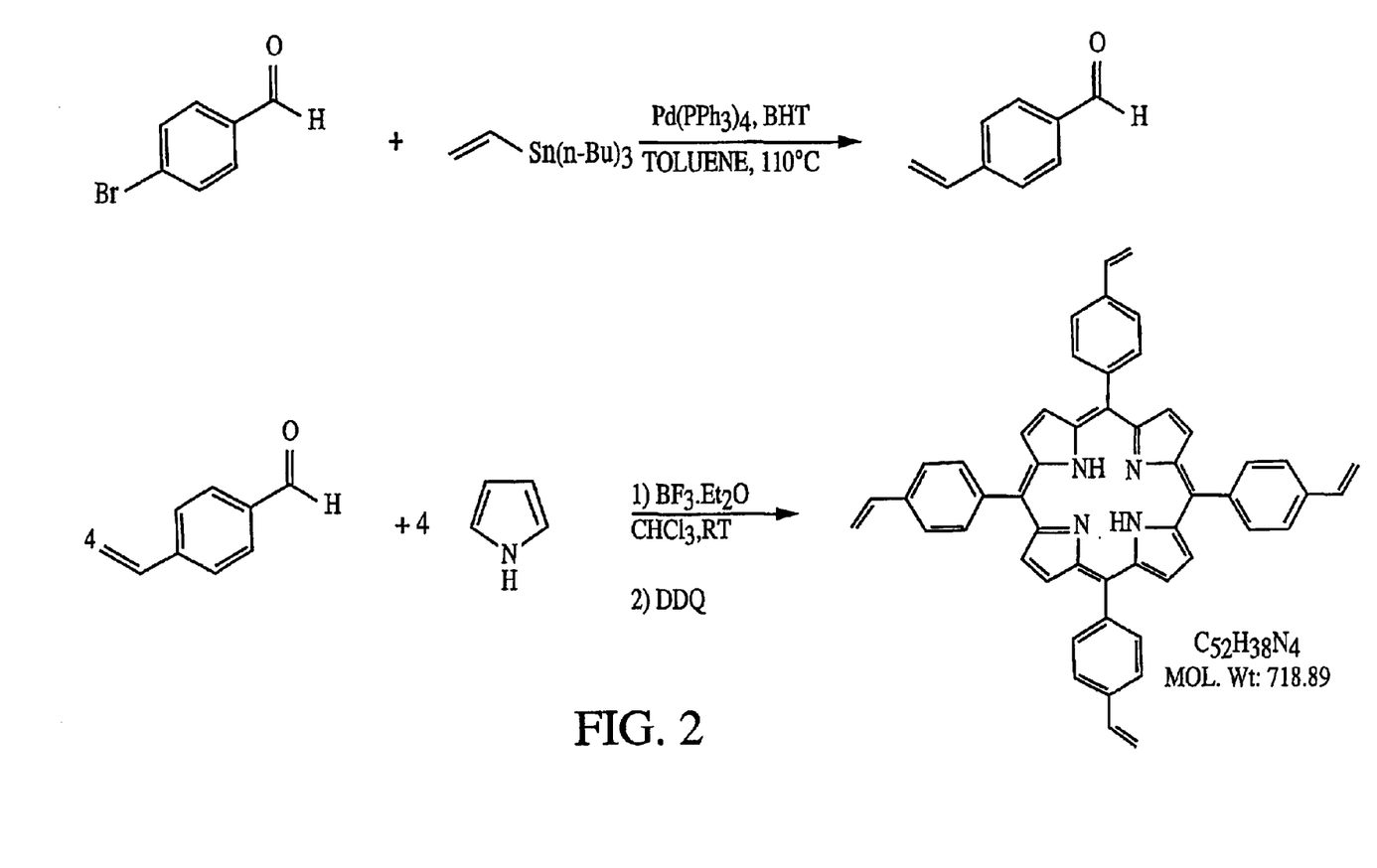
FIG. 2 is a chemical reaction that can be employed to synthesize a polymerizable porphyrin derivative.

In another embodiment, the present invention is directed to a surface acoustic wave sensor for detecting the presence of an explosive in a fluid said sensor having been adapted to comprise a molecularly imprinted polymer having a porphyrin moiety bound thereto. In particular, the surface acoustic wave sensor of the present invention comprises:

a film of a molecularly imprinted polymer of the present invention disposed on a substrate such as alumina or a piezocrystal substance such as quartz crystal, wherein the porphyrin moiety is capable of chemically binding with fluids containing an explosive;

input and output transducers disposed on the film or substrate; and a function generator operatively associated with the input transducer for generating a surface acoustic wave along a delay line. FIG. 2 depicts a sensor device having the features of this embodiment.

Additional aspects, embodiments and advantages of the present invention will be set forth, in part, in the description that follows, or may be learned from practicing or using the present invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

The term "fluid" is used herein in the broadest sense, i.e., as referring to include gases such as vapors and liquids such as, for example, water, solvents, and the like.

BRIEF DESCRIPTION OF THE DRAWINGS

Other objects, features and advantages of the present invention will occur to those skilled in the art from the following description of preferred embodiments and the accompanying drawings, in which.

DESCRIPTION OF THE PREFERRED EMBODIMENTS

References cited throughout this written description are incorporated herein in their entirety to more fully describe the state of the art to which they pertain.

As used herein, the term "molecularly imprinted polymer" and "MIP" refer to a molecular mold-like structure that has preorganized interactive moieties complementing the spacing of binding sites on a target molecule comprising an explosive chemical selected from the group consisting of 2,4,6-trinitrotoluene (TNT) and 1,3,5-trinitrobenzene (TNB). The interactive moieties are porphyrin moieties possessing a geometrical organization which imparts selective binding characteristics for the explosive chemical. The term "selective binding" is intended to refer to preferential and reversible binding exhibited by the MIP herein for the explosives chemical compared to non-template molecules having similar structures, e.g., insecticides such as chloronitro-benzenes. Selective binding includes both affinity and specificity of the MIP for the explosives chemical.

The origins of molecularly imprinted molecules trace back to the notion of Linus Pauling that the body assembled a new protein complement (i.e., an antibody) by using the foreign intruder as a template. Although it was later determined that this is not how antibodies are selected in vivo, this template concept stimulated significant thought and research. Molecular imprinting creates specific recognition sites in materials, such as polymeric organic materials. Known molecular imprinting techniques involve crosslinking materials in the presence of a functional monomer or mixture of monomers. The template molecule interacts with a complementary portion of a functional monomer, either covalently or by other interactions such as ionic, hydrophobic or hydrogen bonding, so that recognition sites for the template molecule can be provided in the substrate material. The template molecule is then removed from the substrate to leave a "cavity" or recognition site. Linus Pauling reasoned that shape specificity was obtained by using a target antigen to arrange the complementary shape of an antibody. Thus, a nonspecific molecule can be shaped to the contours of a specific target, and when the target is removed, the shape is maintained to give the antibody a propensity to rebind the antigen. This process is known as "molecular imprinting" or "templating."

Figure 1:
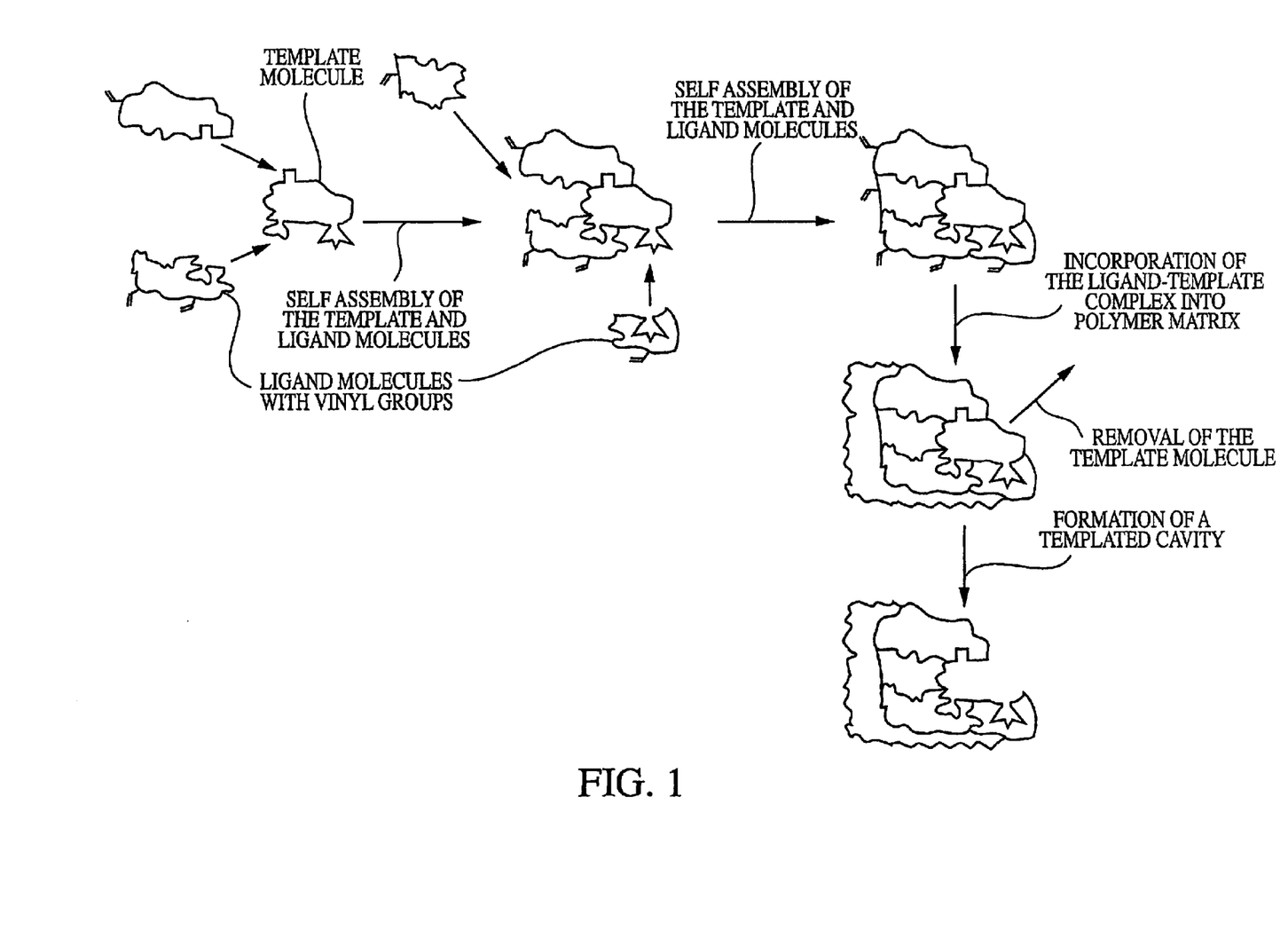
FIG. 1 is a schematic representation of molecular imprinting to obtain a molecularly imprinted polymer of the present invention.

The MIP herein will bind the explosive chemical either covalently or noncovalently, with which it was imprinted with higher affinity then other similar though not identical species. FIG. 1 is a schematic representation of molecular imprinting showing self assemble of explosives chemicals as template molecule and ligand molecules (1,2); incorporation of the ligand-explosives chemical complex into the polymer matrix (3) removal of the explosives chemical; and formation of the templated cavity (5). Methods for preparing MIPs are described in U.S. Pat. Nos. 4,406,792, 4,415,655, 4,532,232, 4,935,365, 4,960,762, 5,015,576, 5,110,883, 5,208,155, 5,310,648, 5,321,102 and 5,372,719, the contents of which are incorporated by reference herein.

An MIP in accordance with the principles of the present invention can be prepared by the steps which comprise:

(A) providing the reaction product of (i) a polymerizable porphyrin derivative and (ii) a target molecule comprising an explosive chemical selected from the group consisting of TNT and TNB;

(B) copolymerizing the reaction product of step (A) with monomer and crosslinking agent to form a polymer; and (C) removing the target molecule from the polymer to provide a molecularly imprinted polymer which exhibits selective binding affinity for the target molecule and undergoes a detectable change in absorption and/or emission of electromagnetic radiation when the target molecule binds thereto. The polymerization reaction mixture for the preparation of the MIP therefore constitutes the reaction product of step (A), one or more polymerizable monomers, an effective amount of one or more crosslinking agents to impart a sufficiently rigid structure to the polymer end-product, inert solvent, and a free radical or other appropriate initiator. Mixtures of monomers and crosslinking agents can be used in the polymerization method.

The polymerizable porphyrin derivative corresponds to the general formula:

wherein $R_1$ is independently a polymerizable moiety selected from the group consisting of styrene, methacrylate, acrylate, vinyl, vinyl ether, vinyl acetate, amine, carboxyl, hydroxyl, trialkoxysilane, dialkoxychlorosilane and epoxy; and $R_2$ is independently H, F, Cl, Br, I, alkyl, heteroalkyl having 1 to 20 carbon atoms, aryl or heteroaryl having from 2 to about 20 carbon atoms, alkenyl or heteroalkenyl having from 2 to about 20 carbon atoms, alkynyl or heteroalkynyl having from 2 to about 20 carbon atoms or trialkylsilyl.

The terms heteroalkyl and heteroaryl are intended to denote moieties wherein a heteroatom is inserted into the carbon backbone of an alkyl or aryl structure (e.g., ether, thioether, and pyridinyl groups). Representative heteroatoms include N, O, S, Se and Te. The terms alkyl, aryl, alkenyl, and alkynyl are intended to include moieties substituted with, for example, halogens or nitro, acid, alkyl, or ester groups. Preferred alkyl and aryl groups have from 1 to about 10 carbon atoms and about 6 to about 14 carbon atoms, respectively. Preferred alkenyl and alkynyl groups have from 2 to about 10 carbon atoms.

Preferred are porphyrin derivatives corresponding to the general formula above wherein $R_1$ each is styrene and $R_2$ each is H.

Methods for synthesizing porphyrin and derivatives thereof are known. See, e.g., Wagner, R. W., Lawrence, D. S. and Lindsey, J. S., Lawrence, D. S. "Studies of Picket Fence Porphyrin and Substituted Metallo-Phthalocyanines", Dissertation, University of Rochester, 1994 and U.S. Pat. Nos. 5,371,199, 5,493,017, 5,599,924, the contents of which are incorporated by reference herein. The synthesis of a preferred porphyrin derivative is depicted in FIG. 2. As shown therein, stoichiometric amounts of 4-vinylbenzaldehyde (synthesized as in McKean, D. R.; Parinello, G.; Renaldo, A. F.; Stille, J. K., "Synthesis of functionalized styrenes via palladium-catalyzed coupling of aryl bromides with vinyl tin reagents" J. Org. Chem., 1987, 52, 422–424 and pyrrole (0.01 M each in chloroform) are reacted with a catalytic amount of boron trifluoride etherate (0.0033 M) at room temperature for 60 minutes to form the reactive intermediate porphyrinogen. This intermediate is then oxidized with 2,3-dichloro-5, 6-dicyano-1,4-benzoquinone (DDQ) to form the derivatized porphyrin which is substituted by polymerizable styrene groups. It will be apparent to those skilled in the art that alternate pathways to synthesizing the product depicted in FIG. 2 are possible, and are within the scope of this invention.

Figure 5A:
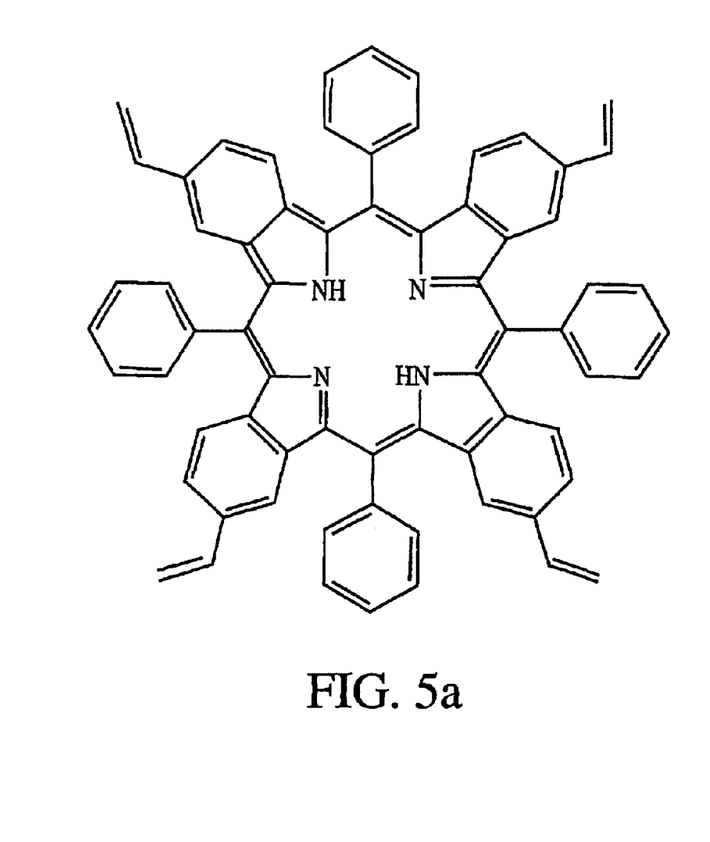
FIGS. 5a and 5b depicts monomers that may be employed in the synthesis of the MIP of the invention.
Figure 5B:
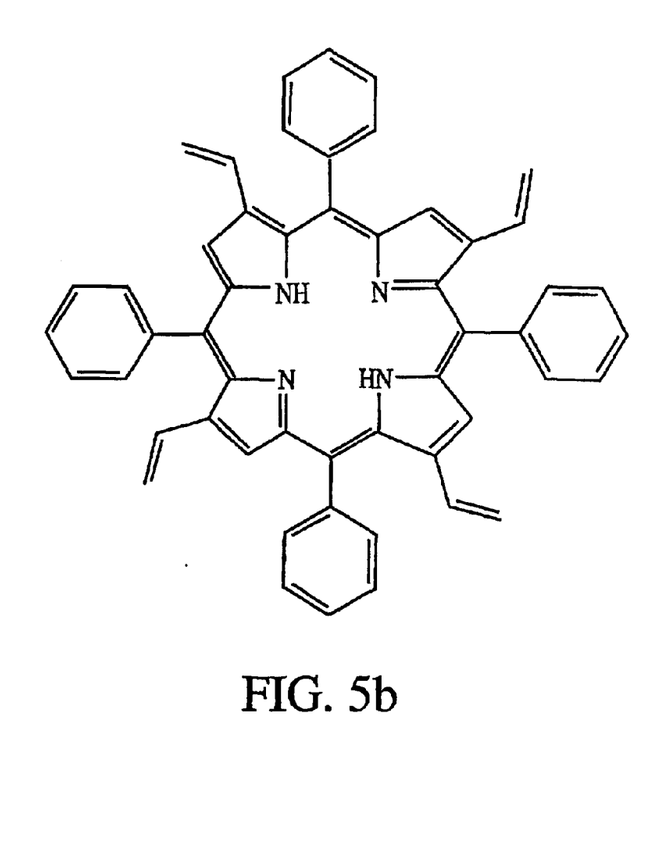

A wide variety of monomers may be used for synthesizing the MIP in accordance with the principles of the present invention. For example, structural representations of preferred monomers are depicted in FIGS. 5a and 5b, namely (a) 5,10,15,20 tetraphenyl-2,7,12,17-tertravinyl porphine, and (b) 1,6,11,16-tetraphenyl-4,8,13,19-tetravinyl-tetrabenzporphine. Examples of other suitable monomers include, but are not limited to, those described in the references cited in this written description and incorporated by reference herein. Further suitable non-limiting examples of monomers that can be used for preparing a MIP of the present invention include methylmethacrylate, other alkyl methacrylates, alkylacrylates, ally or aryl acrylates and methacrylates, cyanoacrylate, styrene, .alpha.-methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-.alpha.-acryloxy-.beta., .beta.'-dimethyl-g-butyrolactone; N-acryloxy succinimide N-acryloxytri.s(hydroxymethyl) aminomethane; N-acryloly chloride; N-acryloyl pyrrolidinone; N-acryloyl-tris (hydroxymethyl)amino methane; 2-amino ethyl methacrylate; N-(3-aminopropyl)methacrylamide; (o, m, or p)-amino-styrene; t-amyl methacrylate; 2-(1-aziridinyl)ethyl methacrylate; 2,2'-azobis-(2-amidinopropane); 2,2'-azobisisobutyronitrile; 4,4'-azobis-(4-cyanovaleric acid); 1,1'-azobis-(cyclohexanecarbonitrile); 2,2'-azobis-(2,4-dimethylvaleronitrile); 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; .beta.-bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; N-t-butylacrylamide; butyl acrylate; butyl methacrylate; (o,m, p)-bromostyrene; t-butyl acrylate; (R)-carvone; (S)-carvone; (−)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1, 1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy) ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2, 2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstyrene; 3,4-dimethylstryene; divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12, 17-tetramethyl-21H,23H-propionic acid disodium salt; 3,9-divinyl-2,4,8,10-tetraoraspiro[5,5]undecane; divinyl tin dichloride; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-

(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; ; lead (II) acrylate; (±)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy) ethyl trimethyl ammonium methylsulfate; 2-methoxy propene (isopropenyl methyl ether); methyl-2-(bromomethyl) acrylate; 5-methyl-5-hexen-2-one; methyl methacrylate; N,N'-methylene bisacrylamide; 2-methylene glutaronitrite; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; alpha.-methyl styrene; t-a-methylstyrene; t-.beta.-methylstyrene; 3-methylstyrene; methyl vinyl ether; methyl vinyl ketone; methyl-2-vinyloxirane; 4-methylstyrene; methyl vinyl sulfone; 4-methyl5-vinylthiazole; myrcene; t-.beta.-nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; tetramethyldivinyl siloxane; trans 3-chloroacrylic acid; 2-trifluoromethyl propene; 2-(trifluoromethyl)propenoic acid; 2,4,4'-trimethyl-1-pentene; 3,5-bis(trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfone (divinylsulfone); vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenylphosphonium bromide (triphenyl vinyl phosphonium bromide); vinyl tris-(2-methoxyethoxy)silane; vinyl 2-valerate and the like.

Acrylate-terminated or otherwise unsaturated urethanes, carbonates, and epoxies can also be used in the MIP. An example of an unsaturated carbonate is allyl diglycol carbonate (CR-39). Unsaturated epoxies include, but are not limited to, glycidyl acrylate, glycidyl methacrylate, allyl glycidyl ether, and 1,2-epoxy-3-allyl propane.

Crosslinking agents that impart rigidity or structural integrity to the MIP are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2-isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, and the like.

While free radical polymerization is preferred, monomers can also be selected that are polymerized cationically or anionically. Polymerization conditions should be selected that do not adversely affect the explosive chemical. Any UV or thermal free radical initiator known to those skilled in the art for free radical polymerization can be used to initiate this method. Examples of UV and thermal initiators include benzoyl peroxide, acetyl peroxide, lauryl peroxide, azobisisobutyronitrile (AIBN), t-butyl peracetate, cumyl peroxide, t-butyl peroxide, t-butyl hydroperoxide, bis(isopropyl)peroxy-dicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethyoxy-2-phenyl-acetophenone, and phenothiazine, and diisopropylxanthogen disulfide.

The choice of monomer and cross-linking agent will be dictated by the chemical (hydrophilicity, chemical stability, degree of cross-linking, ability to graft to other surfaces, interactions with other molecules, etc.) and physical (e.g., porosity, morphology, mechanical stability, etc.) properties desired for the polymer. The polymerization procedures and conditions which are used are conventional. The amounts of polymerizable porphyrin, monomer and crosslinking agents can vary broadly, depending on the specific nature/reactivities of the polymerizable porphyrin, monomer and crosslinking agent chosen as well as the specific sensor application and environment in which the polymer/sensor will be ultimately employed. The relative amounts of each reactant can be varied to achieve desired concentrations of porphyrin in the polymer support structure. The solvent, temperature and means of polymerization (e.g. free radical initiation, γ-radiation) can be varied in order to obtain polymeric materials of optimal physical or chemical features, for example, porosity, stability, and hydrophilicity. The solvent will also be chosen based on its ability to solubilize all the various components of the reaction mixture.

Polymerizations are generally conducted in bulk solution by the free-radical method. Similar methodology can be applied to surface grafting and particle coating with the polymer, as described in "Surface Grafting of Functional Polymers to Macroporous Poly Trimethylolpropane Trimethacrylate," P. K. Dhal, S. Vidyasankar and F. H. Arnold, *Chemistry of Materials* 7, 154–162 (1995) and "Molecularly-Imprinted Polymers on Silica: Selective Supports for High Performance Ligand-Exchange Chromatography," S. D. Plunkett and F. H. Arnold, *J. Chromatogr.* A 708, 19–29 (1995).

For bulk polymerization, typically about 0.10 to about 1.0 weight percent of the polymerizable porphyrin with a stoichiometric equivalent amount of the explosive molecule, about 88 to about 93 weight percent monomer and about 5 to about 10 weight percent cross-linker, and about 1 weight percent of a free radical initiator such as azobia (isobutyronitrile) (AIBN) are dissolved in an aqueous/organic mixed solvent which serves as a porogen to create a porous structure. The solution is heated to 45–60° C. in a sonicator for about 2 hours and transferred to an oil bath at 45–60° C. for 24 hours.

Polymerizations can be carried out by a sol-gel process when an alkoxysilane-type of polymerizable compound is used. In this case, the alkoxysilane metal chelating monomer is mixed with tetramethoxysilane or tetraethoxysilane in aqueous solution. The sol-gel condensation can be conducted in acidic or basic conditions using procedures well known to those practiced in the art.

The morphology and selectivity of the polymer for binding the target molecule may be improved by altering the solvent, polymerization temperature, and choice of crosslinking agent, as described in Sellergren, B., Shea, K. J., "Influence of polymer morphology on the ability of imprinted network polymers to resolve enantiomers," *J. Chromatogr.* A 1993, 635:31–40. In particular, photoinitiation at low temperature should promote high selectivity and strong binding by the polymer of the invention.

After polymerization is complete, the crosslinked polymer can be washed and cut into pieces or ground into powder and extensively eluted with the same solvent used for polymerization to remove any unreacted reagents. The polymer is preferably ground in order to maximize the surface area of the polymer and promote access to the polymer by the eluting solvent. The polymer is preferably cryogenically frozen in liquid nitrogen prior to grinding so that the polymer becomes brittle enough to be ground and to prevent degradation of the polymer by the heat of friction generated during grinding.

Removal of the target molecule leaves a macroporous polymer with complementary molecular cavities which include porphyrin moieties that have specific binding affinity for the target molecule with which the polymer was imprinted. The target molecule comprising explosive chemical is removed from the purified polymer under the mildest conditions possible for the cleavage of the bond between the explosive and the porphyrin. This may be accomplished by washing with a suitable organic solvent, such as alcohol or by using a stream of air heated to 40 to 60° C. for a few minutes.

The MIP of the invention can be prepared in a wide variety of forms ranging from powders to beads to macro structures such as plates, rods, membranes or coatings or other materials. A wide range of sensors can be produced from the polymer of the invention, and the type of sensor will depend on the conditions of use (e.g., spot monitoring, continuous monitoring, process monitoring, etc.).

The invention also provides a method for detecting an explosive, comprising:

exposing the molecularly imprinted polymer of this invention to an environment containing explosives such that vapors and/or particulate emissions from the explosive come in contact with the polymer, and detecting any change in absorption and/or emission of electromagnetic radiation by the polymer, said detected change being indicative of the presence of explosive in, on or in association with said environment.

In a preferred embodiment, MIP may be bound to a suitable substrate, such as, for example, a dosimeter-like badge worn by a person or animal, for the detection of explosive vapors. When the person or animal wearing the badge enters an area containing vapors of an explosive, the vapors of the explosive bind to the molecularly imprinted polymer thereby causing the polymer to absorb and/or emit radiation.

In yet another preferred embodiment, the present invention is directed to a fiber optic sensor device for detecting the presence of a target molecule comprising an explosive such as TNT or TNB as well as analogs and degradents thereof, the sensor comprising:

at least one optical fiber means having a proximal end and a distal end for transmitting light energy, the proximal end being disposed within a probe housing, the molecularly imprinted polymer of this invention which has been imprinted for target molecule disposed on, or bonded to, the distal end of the optical fiber means, wherein the polymer is capable of chemically binding with said target molecule, light source means for generating excitation energy, said light source means operatively associated with said optical fiber means such that said excitation light passes through said optical fiber means, and detection means operatively associated with said optical fiber means, for detecting an absorption and/or emission signal generated by said polymer.

Suitable non-limiting examples of light source means include an argon laser, blue laser, tunable laser, light emitting diode (LED), and the like.

Suitable non-limiting examples of detection means include a spectrophotometer, spectrometer (gas or mass), photomultiplier tube, monochromator equipped with a CCD camera, filters, the naked eye, and the like.

In this embodiment, the portable device may employ a modulated laser diode for excitation and a small photosensor module for detection, with the output going to a microprocessor controlled grated integrator. In addition, an optical multiplex switch may be incorporated into the design so that many sensors can be coupled to one control system, which will allow monitoring of a large area such as found in a building, subway station, shopping mall, airport, etc.

In use, vapors or particulate emissions of an explosive or a liquid containing an explosive, if present, bind to the molecularly imprinted polymer causing it to absorb light in the rear-IR region. Light from the light source means travels along the optical fiber to its distal end where it undergoes a change caused by interaction with the polymer. The modified light returns along the same or another fiber to the detection means which interprets the returned light signal. Detection is based on the change that occurs in the polymer's fluorescence spectrum when vapor of an explosive binds to the polymer.

Optionally, the distal end (working end) of the sensor may be enclosed within a semi-permeable membrane to separate the explosive-containing media being analyzed from the probe. One function of the membrane is to separate, as far as possible, the explosive (i.e., those components in a sample that can bind to the probe) from interferents (i.e., compounds which may be present but are undesirable because they either interfere with the progress of the desired determination reactions or take part in reactions of their own which compete with those of the explosive whose detection is being sought and distort or overwhelm the signals that are to be measured).

In yet another preferred embodiment, the present invention is directed to a SAW sensor for detecting the presence of vapors or particulate emissions of an explosive or liquids containing an explosive. The SAW sensor comprises a molecularly imprinted polymer having a porphyrin bound thereto. In particular, the surface acoustic wave sensor of the present invention, comprises:

- a film of a molecularly imprinted polymer containing a porphyrin disposed on a substrate such as alumina or a piezocrystal substance such as quartz crystal, wherein the lanthanide-complex is capable of chemically binding with vapors of an explosive;
- input and output transducers disposed on the film or substrate; and
- a function generator operatively associated with the input transducer for generating a surface acoustic wave along a delay line.

FIG. 2 depicts a SAW device in accordance with the present invention. In use, the function generator supplies a pulse modulated sine signal to the input transducer. The generated surface acoustic wave is modulated in the same way as the input electrical signal. The acoustic energy is converted again into an electric signal in the output transducer which may be connected to a microcomputer. This signal brings information about the amplitude, phase, frequency and velocity of propagation of the surface acoustic wave on the film. When explosive vapors bind to the porphyrin, the sensor substrate will perturb the surface acoustic wave propagation along a so called delay line, which is then detected using conventional means, such as an LED, microcomputer, etc.

EXAMPLES

The present invention will be further illustrated in the following, non-limiting Examples. The Examples, which exemplify a fiber optic sensor for detecting vapors of are illustrative only and do not limit the claimed invention regarding the materials, conditions, process parameters and the like recited herein.

The sensor described below was designed to measure trinitrobenzene.

Unless otherwise indicated, the reagent materials were obtained from commercial suppliers and used without further purification. Analytical reagent grade chemicals were used along with deionized water to prepare solutions. The reagents used in the synthesis of the porphyrin, such 4-vinylbenzaldehyde, pyrrole, boron trifluoride and 2,3-dichloro-5,6-dicyano-1,4-benzoquinone were obtained from Aldrich (Milwauke, Wis.). Solvents such as dimethoxyethane, toluene, acetone, methanol, and ethanol were obtained from Fisher Scientific (Pittsburgh, Pa.).

Instrumentation. Luminescence was excited using an Omnichrome Model 543-AP-401 Argon Ion Laser (Omnichrome, Chino, Calif.) or by a blue light emitting diode or LED (World Precision Instruments, Sarasota, Fla.). Spectra were collected using an f/4, 0.5 m monochromator (Chromex, Albuquerque, N.Mex.) equipped with a Model ST-6 CCD (Santa Barbara Instruments Group, Santa Barbara, Calif.) using Kestrel Spec Software (Rhea Corporation, Wilmington, Del.). Molecular absorbance spectra were obtained using a Cary 50 UV/VIS spectrophotometer (Varian, Victoria, Australia). Radiative lifetimes and quantum efficiencies were measured using a Quanta Master Spectrophosphorimeter (Photon Technologies Inc., Ontario, Canada). Electron micrographs were obtained using a Topcon DS-701 dual stage scanning electron microscope (SEM) (Topcon, Paramus, N.J. 07652). Metal concentrations were determined using a Hewlett Packard 4500 Series ICP-MS model G1820A (Hewlett Packard, Wilmington, Del. 19808). Graphs and spectra were plotted and calculations performed using Igor Pro Software (WaveMetrics Inc., Lake Oswego, Oreg. 97035).

Example 1

Porphyrin Preparation

The synthesis of a tertrastyrylporphyrin is as depicted in FIG. 2. As shown therein, stoichiometric amounts of 4-vinylbenzaldehyde and pyrrole (0.01 M each in chloroform) are reacted with a catalytic amount of boron trifluoride etherate (0.0033 M) at room temperature for 60 minutes to form the intermediate porphyrinogen. This intermediate is then oxidized with 2,3-dichloro-5,6-dicyano-1,4-benzoquinone (DDQ) to form the derivatized porphyrin which is substituted by polymerizable styrene groups.

Example 2

Polymer Preparation

Polymers were prepared by dissolving 0.10 to 1 weight percent porphyrin and a molar equivilent of trinitrobenzne, 83–88 mole percent styrene and 5–10 weight percent divinylbenzene as a crosslinker into a vial containing 2.0 mL of alcohol. Approximately 1 weight percent of azobisisobutylnitrile (AIBN) was added as an initiator. The resulting solutions were placed in glass vials, purged with nitrogen, and sealed using Parafilm and screw on tops. The resulting solutions were violet-brown in color indicative of the porphyrin. The solutions glowed red when excited with blue light.

The monomer solutions were sonicated for 2–4 hours at 60° C. (Sonication is believed to help maintain homogeneity in the polymer.) Zeng, X.; Murray, G. M. *Separation Science*

*and Technology*, 31:2403–2418 (1996). After sonication, the partially polymerized material was placed in an oil bath at 60° C. and allowed to cure overnight. The resulting block copolymers were ground to expose a larger surface area of the polymer and facilitate the removal of the imprinting molecule. Once ground, the imprint is removed by heating or soaking in alcohol. The removal of the imprinting molecule results in a change in the emmsion spectrum with a loss of intensity in the band at 710 nm and a gain in intensity of the porphyrin band at 660 nm.

Example 3

Fiber Optic Sensor

A procedure for preparing optical substrates for polymer coating was developed for the sensor coatings. A solution of trimethoxystyryl silane in toluene is used to place a chemically bound styrene coating on the surface of optical substrates. Experiments were first performed on microscope slides and have shown that the optimal period of silanization using trimethoxystyryl silane in toluene is about twenty minutes. The surface coverage of the layer is indicated by the contact angle made by a drop of water on the surface of the glass. Dip coating of surfaces prepared by silanization result in films that are chemically bound to the surface.

A fiber optic sensor comprising a 400 micron optical fiber (Thor Labs, Newton, N.J., 07860) with the polymeric sensing element chemically bound on its distal end was constructed. The fibers were prepared by terminating one end with an SMA connector and removing the cladding from and polishing the distal end using the procedures outlined in the "Thor Labs Guide to Connectorization and Polishing of Optical Fibers". The tips were dipped into the chemically initiated viscous copolymer described in Example 2 leaving a uniform layer on the fiber. The polymer finished curing under a UV illuminator, overnight. Coated fibers were conditioned in a manner similar to the ground polymers as outlined above. Final versions of the sensor were prepared using a tapered fiber created by heating it in an air/acetylene flame and manually pulling the stripped end. The tapered fibers were much more efficient at coupling the evanescent field to the polymer and gave greatly improved results.

What is claimed is:

1. A fiber optic device for detecting the presence of target molecules comprising an explosive organic chemical, the sensor comprising:

at least one optical fiber means having a proximal end and a distal end for transmitting light energy, the proximal end being disposed within a probe housing;

a molecularly imprinted polymer formed by the steps of:

(A) providing the reaction product of (i) a polymerizable porphyrin derivative and (ii) a target molecule comprising an explosive organic chemical;

(B) copolymerizing the reaction product of step (A) with monomer and crosslinking agent to form a polymer; and (C) removing the target molecule from the polymer, said polymer exhibiting selecting binding affinity for the target molecule and under going a detectable change in absorption and/or emission of electromagnetic radiation when the target molecule binds thereto;

the molecularly imprinted polymer being disposed on the distal end of the optical fiber means, wherein the polymer is capable of chemically binding with said target molecule;

light source means for generating excitation energy, said light source means operatively associated with said optical fiber means such that said excitation light passes through said optical fiber means; and detection means operatively associated with said optical fiber means, for detecting an emission signal generated by said polymer;

wherein the explosive organic chemical is selected from the group consisting of TNT or TNB.

2. A method for detecting the presence of a target molecule comprising an explosive organic chemical comprising the steps of:

providing a fiber optic sensor device comprising:

at least one optical fiber means having a proximal end and a distal end for transmitting light energy, the proximal end being disposed within a probe housing;

a molecularly imprinted polymer formed by the steps of:

(A) providing the reaction product of (i) a polymerizable porphyin derivative and (ii) a target molecule comprising an explosive organic chemical;

(B) copolymerizing the reaction product of step (A) with monomer and crosslinking agent to form a polymer; and (C) removing the target molecule from the polymer, said polymer exhibiting selecting binding affinity for the target molecule and under going a detectable change in absorption and/or emission of electromagnetic radiation when the target molecule binds thereto;

the molecularly imprinted polymer being disposed on the distal end of the optical fiber means, wherein the polymer is capable of chemically binding with said target molecule;

light source means for generating excitation energy, said light source means operatively associated with said optical fiber means such that said excitation light passes through said optical fiber means; and detection means operatively associated with said optical fiber means, for detecting an emission signal generated by said polymer;

exposing the molecularly imprinted polymer to an environment containing the explosive such that the explosive comes in connect with the polymer, and detecting any change in absorption and/or emission of electromagnetic radiation by the polymer, said detected change being indicative of the presence of the explosive in, on or in association with said environment;

wherein the explosive organic chemical is selected from the group consisting of TNT or TNB.

* * * * *

UNITED STATES PATENT AND TRADEMARK OFFICE
CERTIFICATE OF CORRECTION

PATENT NO. : 6,872,786 B2
DATED : March 29, 2005
INVENTOR(S) : George M. Murray, Bradley M. Arnold and David S. Lawrence It is certified that error appears in the above-identified patent and that said Letters Patent is hereby corrected as shown below:

<u>Title page,</u>
Item [75], Inventors, please insert -- David S. Lawrence, Olney, MD (US) --

<u>Column 13,</u>
Line 45, delete "optic device" and insert therefor -- optic sensor device --

<u>Column 14,</u>
Line 35, delete "under going" and insert therefor -- undergoing --
Line 55, delete "connect" and insert therefor -- contact --

Signed and Sealed this

Seventh Day of June, 2005

JON W. DUDAS
*Director of the United States Patent and Trademark Office*